United States Patent [19]

Drbal

[11] 4,042,152
[45] Aug. 16, 1977

[54] DILUTING APPARATUS

[75] Inventor: Vladimir J. Drbal, Miramar, Fla.

[73] Assignee: Coulter Electronics, Inc., Hialeah, Fla.

[21] Appl. No.: 634,129

[22] Filed: Nov. 21, 1975

[51] Int. Cl.² .......................... B67D 5/52; G01N 1/14
[52] U.S. Cl. .................................. 222/137; 417/518; 73/425.6; 23/259
[58] Field of Search .................. 417/518, 464, 511; 222/137; 73/425.6; 23/259

[56] References Cited

U.S. PATENT DOCUMENTS

| 315,442 | 4/1885 | Powers | 417/518 X |
| 1,643,744 | 9/1927 | Lowenfeld | 417/518 |
| 3,059,586 | 10/1962 | Brailsford | 417/465 |
| 3,640,433 | 2/1972 | Rodth | 222/137 X |
| 3,800,984 | 4/1974 | Phelan | 222/148 X |

FOREIGN PATENT DOCUMENTS 209,210   1/1924   United Kingdom ............... 222/137

Primary Examiner—Robert B. Reeves
Assistant Examiner—Frederick R. Handren
Attorney, Agent, or Firm—Silverman & Cass, Ltd.

[57] ABSTRACT

A diluting apparatus or pump having first and second chambers coaxially formed in a single pivotally mounted block. A first piston is reciprocally disposed in the first chamber and a second piston is coaxially mounted on the first piston and reciprocally disposed in the second chamber, substantially eliminating any transverse thrusts on the pistons. A spool valve is pivotally mounted on an eccentric pin mounted on a rotating crank to drive the pistons. The valve reciprocates within a valve body to couple the first chamber to a fluid supply line on a return stroke and to couple the first chamber to an output line on a delivery stroke. The second chamber is coupled to the output line on both strokes to draw in a second fluid on the return stroke and discharge it with the fluid from the first chamber on the delivery stroke thus mixing the two fluids.

11 Claims, 6 Drawing Figures

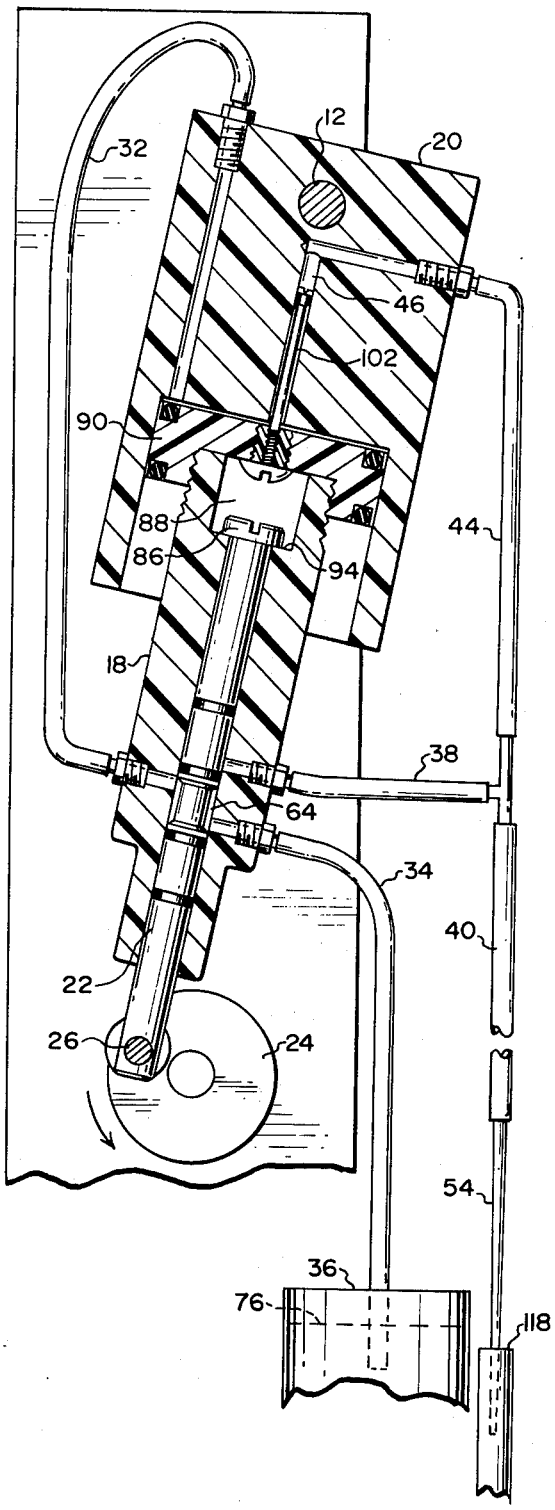

DILUTING APPARATUS

BACKGROUND OF THE INVENTION

The invention relates generally to a diluting apparatus, and more particularly, to such apparatus for use in the analysis and study of body fluids.

In the analysis and study of body fluids, the fluids to be studied usually are diluted prior to performing the analytical procedures required. It is important in the performance of such diluting operations to maintain a precise ratio of sample volume to diluent volume so as to provide for accurate statistical evaluation and analysis of the fluid samples. Various electrical-mechanical devices have been developed to perform such diluting operations. One such electrical-mechanical device is disclosed in U.S. Patent application, Ser. No. 557,681, filed Mar. 12, 1975, now U.S. Pat. No. 3,963,148, entitled "APPARATUS FOR DRAWING, MEASURING AND DISCHARGING PROPORTIONAL AMOUNTS OF FLUID," which is owned by the assignee of the present application. U.S. Patent application, Ser. No. 557,681, now U.S. Pat. No. 3,963,148, is incorporated herein by specific reference to provide background details and disclosure for a diluting apparatus and system including electrical controls, and to provide further background with respect to the operation of such apparatus.

SUMMARY OF THE INVENTION

The present invention provides a pump for mixing a precise amount of two fluids to produce a measured dilution of one of the fluids. The pump has two pistons, an upper smaller one mounted astride a lower larger one, each piston disposed for reciprocal movement in a coaxial chamber. The pistons are concentrically mounted to substantially eliminate any transverse thrusts as they reciprocate. The size of the two pistons and chambers is chosen such that a precise volume ratio is maintained between the fluids in the two chambers. The lower piston is mounted on a spool valve body which has a spool valve reciprocally mounted therein to move between a first piston delivery position and a second piston return position. The spool valve is coupled to the lower piston's chamber coupling said chamber to a first fluid supply in said return position and coupling said chamber to an output line in said delivery position. The lower end of said spool valve is mounted on a rotating crank by means of an eccentric pin to provide the valve and piston reciprocation. The second smaller chamber is coupled only to said output line. Said output line is immersed in a second fluid on said piston return stroke to draw in a discrete volume of said second fluid on said return stroke and said output line is positioned in a test vessel on said piston delivery stroke to discharge and mix said discrete volume of said second fluid with said first fluid from said first fluid supply by the delivery stroke of said pistons. Said pistons and chambers are formed in a pivotally mounted block to allow the valve and pistons to follow the path defined by the eccentric pin mounted on the rotating crank.

BRIEF DESCRIPTION OF THE DRAWINGS

FIG. 5 is a similar view to that of FIG. 3 illustrating the valve of the diluting apparatus in a return position; and FIG. 6 likewise is a similar view showing the apparatus in a completed return position.

DESCRIPTION OF THE PREFERRED EMBODIMENT

Figure 1:
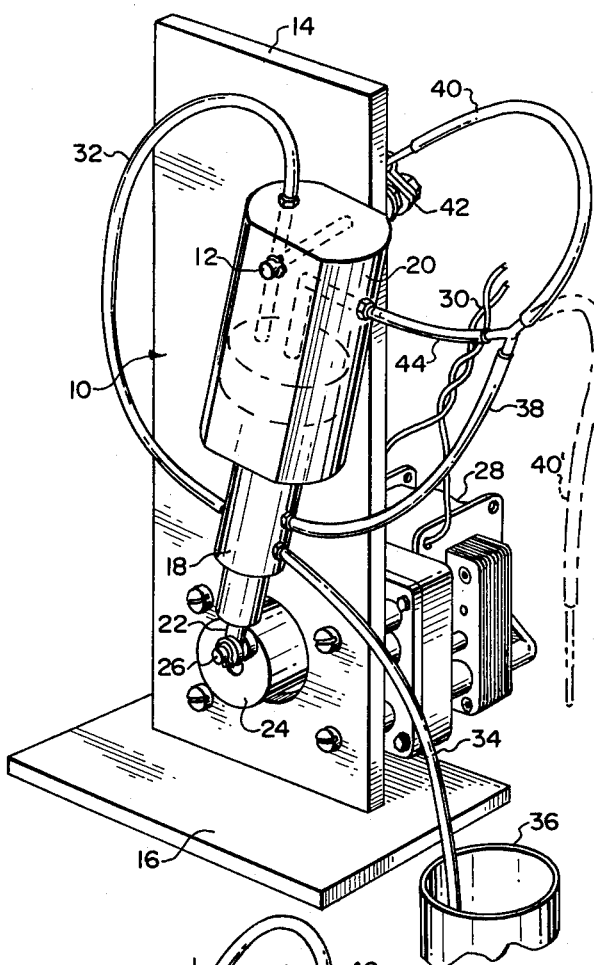
FIG. 1 is a perspective view of the diluting apparatus with drive motor of the invention.

Referring to FIG. 1, the diluter or pump designated generally by the numeral 10 is pivotally mounted on a pivot pin 12 to any convenient vertical support surface, such as a plate 14 mounted on a base 16. A piston 90 is mounted on a spool valve body 18 and reciprocates within a pump body 20. The spool valve body is driven by a spool valve plunger 22 pivotally mounted on a rotating crank 24 by an eccentric pin 26. Preferably the pivot pin 12 and the eccentric pin 26 are mounted perpendicular to the plate 14 and parallel to one another. However, to compensate for any imperfections in the alignment of the two pins, the eccentric pin 26 has a double sleeve (not shown) with an inner layer made of any convenient flexible material, such as an elastomer.

A motive source as, for example, an electric motor 28 energized by a power line 30 provides the rotational drive for the crank 24. The electric motor 28 may be controlled by a manual switch (not shown) in power line 30 or may have an automatic control designed for a particular operation. Automatic control circuitry for a diluting system is disclosed in U.S. Patent application Ser. No. 557,681, incorporated herein.

A first conduit 32 connects a first chamber 120 (FIG. 6) to the spool valve body 18 and through said spool valve body in a first position to a supply conduit 34 shown disposed in a fluid supply vessel 36, and through said valve body in a second position to an output conduit 38 connected to a probe conduit 40. The probe conduit is shown in solid lines inserted in a bracket 42 for storage when not in use. The bracket 42 is shown mounted on pivot pin 12, but it could, of course, be mounted in any convenient location or even deleted. The probe conduit is shown at 40' removed from bracket 42 ready for use. A second conduit 44 connects a second chamber 46 (FIG. 3) to probe conduit 40.

Figure 2:
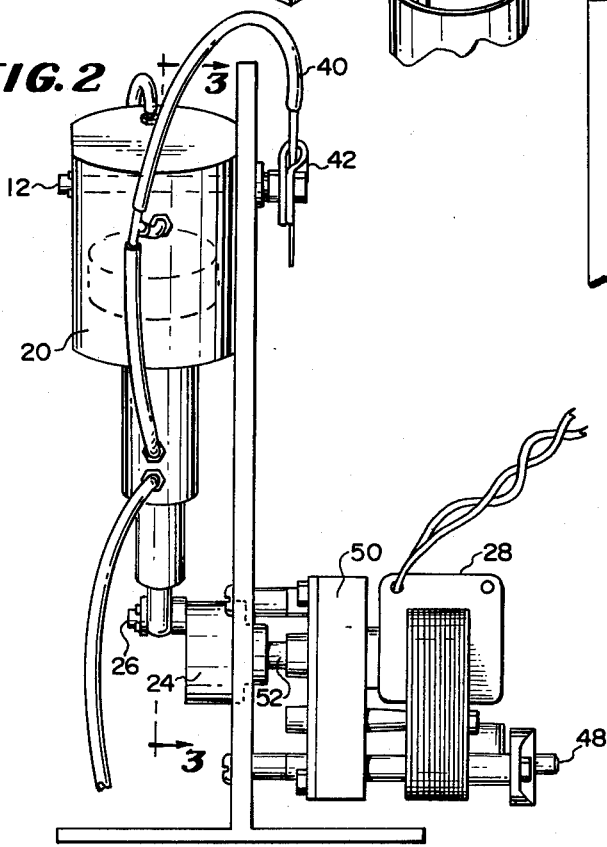
FIG. 2 is a side elevational view thereof.

Referring now to FIG. 2, the storage bracket 42 may more clearly be seen mounted on the end of pivot pin 12. The storage position of the probe conduit 40 also is illustrated more clearly. The motor 28 drives a shaft 48 at a predetermined speed which may not be suitable for a particular operation, and consequently a shaft 48 may be coupled to a gear box 50 to provide the proper speed for a drive shaft 52 upon which crank 24 is mounted. By properly sizing the motor and gear box, an optimum speed and power output are attainable.

The diluter or pump body 20 preferably is formed of a one-piece lightweight polymer material which is transparent to enable observation of the operation of the apparatus; and to provide a visual check for malfunctions. The conduits associated with body 20 also preferably are transparent for the same reason; however, any suitable materials may be used.

Figure 3:
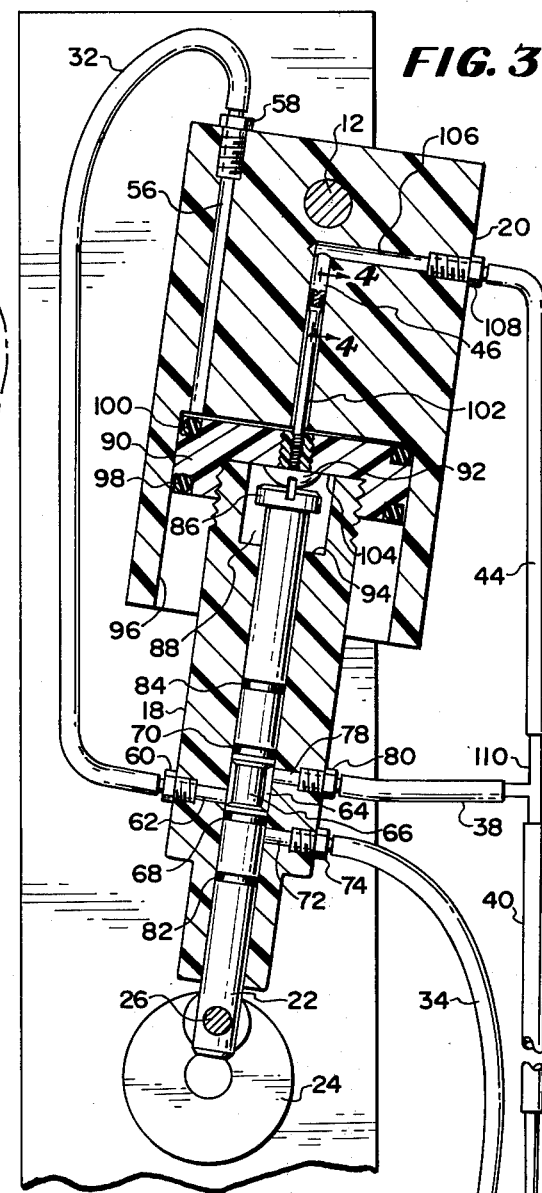
FIG. 3 is a sectional view taken along the line 3—3 of FIG. 2 in the direction indicated generally illustrating the diluting apparatus in a completed delivery position thereof.

Referring to FIG. 3, probe conduit 40 includes a probe 54 to be immersed in a body of fluid. The first chamber 120 (FIG. 6) is connected to conduit 32 at a fitting 58 mounted at the terminus of a first channel 56 formed in the pump body 20. The opposite end of conduit 32 is connected at a fitting 60 mounted in spool valve body 18 to a first channel 62 formed in the spool valve body. Channel 62 couples conduit 32 to a valve chamber 64 formed by a spool portion 66 of spool valve plunger 22. The spool valve is a convenient choice, as it couples the appropriate chambers and conduits and automatically switches positions prior to the movement of the pistons, with a minimum number of parts and space. However, it should be noted that other valving, such as a solenoid or rotary valve, can be utilized in lieu of the spool valve. The valve chamber is sealed from leakage between supply conduit 34 and output conduit 38 by seals 68 and 70. The seals may be standard O-rings of any suitable material.

The valve chamber 64 connects conduit 32 to a second channel 72 formed in the spool valve body 18 when the spool valve plunger is moved to its return position (FIG. 5) and hence through a fitting 74 mounted in the spool valve body to the supply conduit 34 which is immersed in a body of supply fluid 76 such as a diluent in vessel 36. In its delivery position, the valve chamber 64 connects conduit 32 through a third channel 78 to output conduit 38 at a fitting 80 mounted in the spool valve body. Two more O-ring seals 82 and 84 seal the fluid present in channels 72 and 78 and prevent leakage in either direction along the spool valve plunger.

The spool valve plunger 22 also has a plunger head 86 of greater diameter than that of the spool valve body. The plunger head 86 is positioned in a space 88 which has sufficient height to allow plunger head 86 to reciprocate a sufficient distance to complete the connection of the valve chamber 64 to the delivery and supply positions described above. The space 88 has a bottom shoulder 94 which forms a stop for the plunger head 86 in the return position. The piston 90 reciprocates within a chamber wall 96 formed in the pump body 20 which defines the first chamber 120. The piston may be sealed against the chamber wall by any convenient means. In the embodiment shown, a circular channel is made in the top and bottom of the piston leaving a thin outer wall, O-rings 98 and 100 are then force-fit into the channels sealing the thin outer piston walls against the chamber wall. A second piston 102 concentrically is mounted on piston 90 to reciprocate in the second chamber 46. The alignment and support provided by the concentric mounting of the second piston on the first piston, substantially eliminates any transverse thrusts against the pistons and the spool valve body as they reciprocate. The second piston may be mounted in various ways as with a screw 92. If piston 102 is mounted with screw 92 then the screw instead of a bottom 104 of the piston 90 will form the stop for plunger head 86 in the delivery position. The second chamber 46 is connected through a second channel 106 formed in the pump body at a fitting 108 mounted in the pump body to the second conduit 44 and through a "T" connector 110 to output conduit 38, probe conduit 40, and to probe 54.

Figure 4:
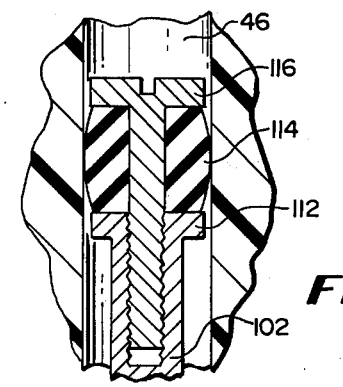
FIG. 4 is a sectional view of the second piston head taken along the line 4—4 of FIG. 3 in the direction indicated generally.

Referring to FIG. 4, further details of the second piston 102 can be seen, including a flange 112 on top of the piston forming a support for a seal 114. The seal 114 is compressed to a proper sealing fit in chamber 46 and adjusted for wear by adjusting the tension applied thereto. A screw 116 may be mounted in the end of the piston 102 to apply the tension to the seal 114.

A typical operation of the diluting apparatus through one full cycle thereof will now be described with reference to FIGS. 3, 5 and 6. Although the operation will be described in connection with a diluting system, it is to be understood that the invention is such that it is adaptable for use with many other pumping systems. The pump is first primed by filling the whole system with diluent and excluding all air from the system including that which may be present in conduits 32, 34, 38, 40, 44 and probe 54. The probe 54 is then inserted in a first body of fluid sample such as blood contained in a sample vessel 118 (FIG. 5) and the pump is started from a top dead center position of the eccentric 26 (the end of the delivery stroke) as shown in FIG. 3. As the crank 24 and the eccentric 26 rotate they first draw the spool valve plunger 22 down until plunger head 86 bears against shoulder 94 of space 88 as shown in FIG. 5. The valve chamber 64 is correspondingly drawn from its delivery position (FIG. 3) to its return (aspirating) position. This movement connects the first chamber 120 through conduit 32, valve chamber 64 and supply conduit 34 to supply fluid 76 which is the same diluent as the system was initially filled with. The second chamber 46 is connected at all times to conduit 44, output conduit 38, probe conduit 40 and probe 54. As the crank and eccentric continue rotating the plunger head 86 will now pull the spool valve body 18 including piston 90 and piston 102 in a downward direction. As piston 90 is pulled downward, the diluent 76 will flow upward through supply conduit 34, valve chamber 64, and conduit 32 into chamber 120. The corresponding downward movement of piston will draw a volume of the sample to be diluted or mixed in sample vessel 118 up into the probe 54. The volume of sample will correspond to the finite volume of diluent which was displaced by piston 102 in chamber 46 between the end of its return stroke (bottom position) as shown in FIG. 6 and the end of its delivery stroke (top position) as shown in FIGS. 3 and 5. A precise ratio of diluent to sample is attained by the proper sizing of piston 90, chamber 120, piston 102, and chamber 46. The volume ratio may be chosen for the particular fluids involved, and in practice has varied from a ratio of 1:4 to 1:250. The volume ratio could, of course, be less or greater than these figures as desired. This return or aspirating stroke is completed when the crank and eccentric reach their bottom dead center position as shown in FIG. 6. At this bottom position the pump is manually or automatically stopped and the probe 54 is moved manually or automatically from sample vessel 118 to a test vessel 122 (FIG. 6). The probe 54 could also be moved manually or automatically at the proper moment in the pump cycle (with the eccentric 26 at or just past bottom dead center) from sample vessel 118 to test vessel 122 without stopping the pump motor 28.

The delivery or discharge stroke next is initiated by starting the pump if it has been stopped causing the crank and eccentric to continue rotating. As the crank and eccentric start upward they push up against spool valve plunger 22 driving the spool valve plunger and the plunger head 86 upward through the spool valve body 18 and space 88 until the plunger head 86 comes in contact with the screw 92 as shown in FIG. 3. At this point spool valve body 18 is still in its bottom position as shown in FIG. 6. The valve chamber 64 is correspondingly pushed upward from its return position to its delivery position. This movement connects the first chamber 120 (now filled with diluent) through conduit 32, valve chamber 64, output conduit 38, probe conduit 40 and probe 54 into the test vessel 122. The second chamber 46 also is connected to probe conduit 40 and probe 54 through lines 44. As the crank and eccentric continue rotating, plunger head 86 will drive spool valve body 18 including piston 90 and piston 102 in an upward direction. As piston 90 is pushed upward the diluent contained in chamber 120 will be delivered through conduit 32, valve chamber 64, output conduit 38, probe conduit 40 and probe 54 into the test vessel 122. At the same time a corresponding movement of piston 102 forces the diluent out of chamber 46 through conduit 44 into probe conduit 40 and probe 54. The diluent from both output conduit 38 and conduit 44 will force the finite sample volume from the probe 54 into the test vessel 122, and flush the conduits and probe so a new sample will not be contaminated.

The delivery stroke is completed when the crank and eccentric have rotated to their top dead center position as shown in FIG. 3. At the top position the pump is again stopped manually or automatically and the probe 54 is moved manually or automatically into another sample vessel. If desired, it could, of course, be left in the first sample vessel for another cycle. The probe 54 also could be moved at the proper point without stopping the pump (with the eccentric 26 at or just passed top dead center) as was previously noted. The pump is now ready for another cycle of operation to be initiated.

It can clearly be seen from the above description that a finite amount of sample has been taken in through probe 54 and this same finite sample has been delivered along with a precise predetermined volume of diluent. The analytical procedures necessary to evaluate and analyze the sample can now be undertaken with the precise ratio of sample volume to diluent volume delivered by the pump.

FIGS. 3, 5 and 6 also clearly illustrate another advantage of the present invention. A minimum number of parts are connected to the crank 24 and eccentric 26 by pivotally mounting the pump body 20 on pivot pin 12 and the spool valve plunger 22 on eccentric 26. As the crank and eccentric rotate the pump body and spool valve assembly freely pivot on their mountings without adding further followers. This allows the spool valve plunger 22 to move a distance to the left and right equal to the distance between the center of crank 24 and the center of the eccentric pin 26. This results in a more reliable pump because of the fewer number of parts required and also a pump which may be mounted in a smaller, hence more efficient space. As previously noted, the alignment and support provided by the concentric mounting of the second piston on the first piston, substantially eliminates any transverse thrusts against the pistons and the spool valve body as they reciprocate.

Modifications and variations of the present invention are possible in light of the above teachings. It is therefore to be understood that within the scope of the appended claims the invention may be practiced otherwise than as specifically described.

What it is desired to secure by Letters Patent of the United States is:

I claim:

1. A diluting apparatus comprising:
   at least a first chamber;
   first piston means reciprocally disposed within said first chamber for moving a first fluid into and out of said chamber;
   piston drive means for reciprocating said first piston means including valve means coupled at least to said first chamber for providing valving to said first chamber as said first piston means reciprocates;
   at least a second chamber disposed coaxial with said first chamber; and
   second piston means reciprocally disposed within said second chamber for moving a second fluid into and out of said second chamber, coaxially mounted on said first piston means, and coupled to said piston drive means;
   whereby transverse thrust against said piston drive means during reciprocal movement of said piston means is substantially eliminated.

2. A diluting apparatus as described in claim 1 wherein:
   said first chamber is pivotally mounted on an axis perpendicular to the path of movement of said first piston means.

3. A diluting apparatus as described in claim 1 wherein said piston drive means further include:
   motive drive means including a rotating crank with eccentric means mounted on said crank engaging said valve means for reciprocating said valve means and said first and second piston means.

4. A diluting apparatus as described in claim 1 further including:
   a single pivotally mounted chamber block having said first and second chambers formed therein.

5. A diluting apparatus as described in claim 1 wherein:
   said valve means are reciprocally mounted within said first piston drive means.

6. A diluting apparatus as described in claim 5 wherein said valve means include:
   a single spool valve plunger having a first drive position coupling said first chamber with a first line and a second return position coupling said first chamber with a second line.

7. A diluting apparatus as described in claim 6 wherein said piston drive means further include:
   motive drive means including a rotating crank with eccentric means mounted on said crank engaging said spool valve plunger for reciprocating said spool valve plunger and said first and second piston means.

8. A diluting apparatus as described in claim 6 wherein:
   said second chamber is coupled to said first line.

9. A diluting apparatus as described in claim 7 further including:
   a single pivotally mounted chamber block having said first and second chambers formed therein.

10. A diluting apparatus as described in claim 9 wherein:
    said chamber block is mounted on an axis perpendicular to the path of movement of said first and second piston means, said axis being substantially parallel to the axis of said rotating crank.

11. A diluting apparatus for handling a fluid sample and a diluent in selective amounts and thereafter discharging the sample and the diluent as a solution of predetermined dilution, said apparatus comprising:
    a first chamber having a first port and conduit means for connecting said chamber to a source of said diluent and a second port and conduit means for discharging diluent in said chamber;
    first piston means reciprocally disposed in said first chamber for moving said diluent into and out of said chamber;

a second chamber having a third port and conduit means for connecting said chamber to said fluid sample and to said second port and conduit means;

second piston means reciprocally disposed in said second chamber for moving said fluid sample into and out of said second chamber, coaxially mounted on said first piston means to substantially eliminate sidewise thrust during said reciprocation of said first and second piston means;

piston drive means for reciprocating said first and second piston means;

valve means operatively connected between said first chamber and said piston drive means for connecting said first chamber to said first port and conduit means in a first position and to said second port and conduit means in a second position as said first and second piston means reciprocate said valve means including a single spool valve plunger reciprocally mounted within said piston drive means;

a single chamber block having said first and second chambers coaxially formed therein pivotally mounted on an axis perpendicular to the axis of movement of said first and second piston means; and rotary crank means having an axis of rotation substantially parallel to said chamber block pivot axis including eccentric means engaging said spool valve plunger for reciprocating said spool valve plunger and said first and second piston means;

whereby said sample is drawn into said third port and conduit means and said diluent is drawn into said first port and conduit means and said first chamber as said piston means reciprocate in a first direction and said diluent is discharged through said second port and conduit means along with said sample as said piston means reciprocate in a second direction opposite said first direction.

* * * * *